United States Patent [19]

Braun et al.

[11] Patent Number: 4,523,695

[45] Date of Patent: Jun. 18, 1985

[54] SURGICAL STAPLER

[75] Inventors: Karl Braun, Talheim; Jürgen Fetzer, Gerstetten-Dettingen, both of Fed. Rep. of Germany

[73] Assignee: Intermedicat GmbH, Emmenbrucke, Switzerland

[21] Appl. No.: 465,354

[22] Filed: Feb. 9, 1983

[30] Foreign Application Priority Data

Feb. 10, 1982 [DE] Fed. Rep. of Germany ..... 32045220

[51] Int. Cl.³ ............................................. A61B 17/04
[52] U.S. Cl. ......................................... 227/8; 227/19; 227/DIG. 1; 227/121
[58] Field of Search .................... 227/19, 83, 121, 120, 227/DIG. 1, 155, 8

[56] References Cited

U.S. PATENT DOCUMENTS

| | | | |
|---|---|---|---|
| 4,180,196 | 12/1979 | Nueil et al. | 227/DIG. 1 |
| 4,185,762 | 1/1980 | Froehlich | 227/DIG. 1 |
| 4,202,480 | 5/1980 | Annett | 227/DIG. 1 |
| 4,204,623 | 5/1980 | Green | 227/DIG. 1 |
| 4,256,251 | 3/1981 | Moshofsky | 227/DIG. 1 |
| 4,364,507 | 12/1982 | Savino | 227/83 |

FOREIGN PATENT DOCUMENTS

| | | | |
|---|---|---|---|
| 1957334 | 5/1971 | Fed. Rep. of Germany | 227/DIG. 1 |
| 815658 | 7/1959 | United Kingdom | 227/DIG. 1 |
| 189982 | 1/1967 | U.S.S.R. | 227/DIG. 1 |

*Primary Examiner*—Paul A. Bell
*Attorney, Agent, or Firm*—Kenyon and Kenyon

[57] ABSTRACT

A stapler, particularly for suturing skin wounds or incisions, is disclosed which comprises a channel in which a driver is advanced by a slide in the direction of an anvil surface. A staple magazine which extends substantially parallel with the driver includes a curved section which opens into the channel to deliver staples into the channel for engagement by the driver. During forward displacement of the driver, a projection on the driver presses a leaf spring to which the anvil surface is connected. The anvil surface at the forward end of the leaf spring is thereby brought into its operating position and is automatically moved back into its retracted position upon release of the spring after the driver is retracted. The curved section in the staple magazine enables the stapler to have a slim profile which does not obscure the working area during a stapling operation. After completion of a stapling operation, the anvil surface is automatically retracted from a closed, implanted staple.

16 Claims, 12 Drawing Figures

SURGICAL STAPLER

BACKGROUND OF THE INVENTION

The present invention relates to a surgical stapler for applying staples to suture or close a wound or incision, particularly a surgical skin stapler for implanting skin staples in or through the skin to suture an exterior wound or incision.

Surgical staplers are used for closing or connecting conformed wound edges of tissue by implanting metal staples in the tissue. By actuation of a lever, the staple is pressed by a ram or driver against an anvil surface provided at the tip of the stapler tool and is thereby deformed, so that the parts of the staple protruding from the stapler tip are moved toward each other and penetrate into the tissue.

U.S. Pat. No. 4,179,057 discloses a surgical stapler comprising a staple magazine containing a supply of staples, a spring for advancing the staples in the staple magazine, an anvil surface provided at the stapler tip, and a driver displaceable relative to the anvil surface in a staple channel which deforms a staple supported on the anvil surface. In a stapler of the type disclosed in the aforementioned patent, the staples are advanced along a straight feed path in the staple magazine. The forwardmost staple lies in the path of movement of the driver which extends at an angle which appears to be about 50° with respect to the longitudinal axis of the staple magazine. The stapler is actuated in plier fashion to advance the driver which presses the forwardmost staple protruding from the stapler tip against the anvil surface and deforms it to close the staple side portions. At this point, the staple has been implanted and it is necessary to remove from the staple the anvil surface which is fixed to the stapler tip. However, if the stapler has been improperly positioned, it is possible to pull the closed staple out of the tissue when disengaging the anvil surface from the implanted staple.

U.S. Pat. No. 4,202,480 discloses a surgical stapler which also comprises a staple magazine having a straight staple feed path. The staple channel in the stapler in which the driver is displaceable and the staple magazine meet at almost a right angle. The forwardmost staple is advanced by the driver to the anvil surface on which it is deformed with its side portions protruding forwardly of the stapler tip. The anvil surface is transversely disposed at the forward end of the staple channel. It is also difficult to pull the anvil surface of this stapler out of an implanted staple.

U.S. Pat. No. 3,819,100 discloses a surgical stapler comprising a removable staple cartridge which is inserted into and locked to the stapler. The staple cartridge has a straight staple feed path. Staples are advanced by a driver moved by a stepping mechanism. The forward housing portion of the stapler, into which the staple cartridge is inserted, is rotatable relative to the rear housing portion. The anvil surface is fixed at the front end of the staple cartridge.

Prior art surgical staplers have the disadvantage that they did not afford a good view of the work area because the driver moved transversely to the straight staple magazine. Therefore when the stapler was positioned for use, a considerable portion of the work area was obscured. While it is possible to arrange and feed the staples laying flat one behind the other in order provide a slim tool tip affording a better view of the work area, the cost of manufacturing the parts required to accomplish this is high. Moreover, the number of staples that can be accommodated in a staple magazine if the staples lie flat one behind the other is relatively small.

OBJECTS AND SUMMARY OF THE INVENTION

It is an object of the present invention to provide a surgical stapler, particularly a skin stapler, which eliminates the possibility of tearing an implanted staple out of the tissue or substantially disturbing it when the anvil is separated from the staple, particularly if the stapler was improperly positioned.

The above and other objects are achieved according to the invention disclosed herein which provides a surgical stapler having an anvil surface or nose movable transversely with respect to a staple channel between an operating position and a retracted position, and in which movement of the anvil surface is controlled as a function of the position of a driver in the staple channel which cooperates with the anvil surface to deform a staple.

According to the invention, movement of the anvil surface is coupled with that of the driver. When the driver is moved into its operating position, the anvil surface is also automatically brought into its operating position in which it protrudes into the staple channel in which the driver moves. Advancement of the staple in the channel is stopped by the anvil surface, and deformation of the staple takes place between the anvil surface and the driver. When the driver is subsequently retracted, the anvil surface moves automatically into its retracted position, so that the closed staple does not interfere with removal of the stapler instrument. According to the invention, the anvil surface and the driver are brought into their operating positions together, the driver moving longitudinally in the staple channel while the anvil moves transversely to the staple channel.

Further objects of the present invention are to provide a stapler, particularly a skin stapler, whose tool tip is narrow and in which the staples are arranged and fed upright one against the other so that the staple magazine including the advancing mechanism can be relatively simple and yet the tool tip can be narrow, thereby covering up as little of the work area as possible. These and other objects are achieved in accordance with the invention by providing a staple magazine which extends essentially parallel to the staple channel and having at its forward end a curved section opening into the staple channel.

According to the invention, the staples are disposed in the magazine parallel to each other standing upright so that the side and the base or crown portions of adjacent staples are in contact, and are advanced by a spring. Since the forward end of the staple magazine is curved where the staple magazine opens into the staple channel, the forwardmost staple enters the staple channel in which the driver moves lying flat in the staple channel. When the driver is moved to its operating position, it blocks the opening of the magazine into the staple channel so that the next staple can be advanced into the channel only after the driver has been brought back into its retracted position. Therefore, only the forwardmost staple in the magazine can be engaged by the driver as the driver is moved past the magazine opening.

According to a preferred embodiment of the invention, the anvil surface is fastened to a leaf spring which extends in the staple channel and includes an inclined surface. The driver includes a projection which cooperates with the inclined surface so that when the projection strikes the inclined surface, the leaf spring is deformed in such a way that the anvil surface is brought into its operating position. Upon release of the driver, the tension of the deformed leaf spring is released to automatically return the anvil surface into its retracted position.

For skin staplers precise guiding of the staple during the staple closing process is very important because the staple is closed as it emerges from the staple channel at the tip of the tool. According to a preferred embodiment of the invention, a notch or slot for retaining the base or crown portion of the staple during the deformation process is disposed in the anvil surface. In the initial phase of deformation, a projection or bulge in the base of the staple penetrates into the notch or slot, so that the staple is prevented from turning or pivoting. Preferably the notch or slot is located in the center of the anvil surface and the projection or bulge is symmetrically disposed in the staple. The notch or slot edges preferably dig into the staple and bring about an interlocking of the staple and the anvil surface in the central portion of the base region of the staple.

According to a preferred embodiment of the invention, the staple channel comprises side, upper and lower guide surfaces which limit movement of the forwardmost staple as it is advanced lying flat in the staple channel. The guide surfaces extend forwardly to beyond the anvil surface. An embossment positions the forwardmost staple in the staple channel upon being advanced from the magazine. From there, as the driver is advanced towards its operating position, the staple is transported to the anvil surface and feeding of additional staples from the magazine is blocked. The guide surfaces provide a well-defined advance of a staple in the channel. Preferably the guide surfaces are extended in projections of relatively small dimensions protruding forwardly beyond the anvil surface.

A two-part housing comprising a rear housing portion and a front housing portion which is rotatable relative to the rear housing portion facilitates use of the stapler. The rear housing portion contains the actuating mechanism for the driver and the front housing portion contains the driver and anvil surface which are rotatable together with the front housing portion relative to the rear housing portion. By making the front housing portion rotatable relative to the rear housing portion, the orientation of the staple relative to the actuating mechanism can be selected freely. Hence the physician need not align the actuating mechanism transversely to the wound or incision seam but can hold the instrument in the position most favorable for working the instrument.

It is important that the stapler be actuated with little effort since the instrument can only be held steady and firmly, which is required for precise setting of the staples, if the staples can be deformed and implanted with little physical force. To achieve this, the actuating element of the actuating mechanism and a lever in the rear housing portion, and the driver are coupled in such a way that the effective leverage of the lever increases as the actuating element moves further away from its inoperative position while at the same time the advancing force transmitted to the driver increases for a constant actuating force at the actuating element. In the first phase of actuation of the actuating element, the forwardmost staple of the staple magazine is simply advanced in the staple channel until it reaches the anvil surface. In this first phase the force required is relatively low. However, the maximum force that is available is required when the staple is being deformed and this maximum force occurs when the actuating element reaches its maximum travel. The amount of force required to deform the staple is reduced by the actuating mechanism disclosed herein so that it is possible to deform the staple simply by moving the actuating element with one's index finger. Compared with known staplers, the actuating force required to operate the stapler disclosed herein is reduced by about one half.

It is possible to positively couple the movement of the driver with the lengthwise movement of a slide coupled to the actuating element. However such coupling of the driver to the actuating element would be disadvantageous because the driver would follow every movement of the slide and it is possible that a second staple could enter the channel without the first staple having been deformed and released if the driver is not fully advanced to its operating position. To avoid this, according to the invention, the driver and slide are not positively coupled. Instead means are provided so that the driver is not retracted by the slide unless the driver has been advanced to its operating position. According to a preferred embodiment of the invention, a slide coupled to the actuating element is provided which includes a tongue loaded with a transverse spring action which cooperates with a control cam disposed in the housing. The tongue includes a surface which is positioned against a transverse edge of the driver and permits the driver to be retracted only after the driver has been advanced fully into its operating position. Only then can the driver be retracted and the opening of the staple magazine into the channel cleared so that the next staple can be advanced.

According to a preferred embodiment of the invention, a counting mechanism is provided which is advanced by a projection on the tongue of the slide. The counting mechanism indicates the number of staples used or the number of staples remaining in the magazine.

The above and other objects, features, aspects and advantages of the invention will be more readily perceived from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like numerals indicate similar parts and in which.

DESCRIPTION OF THE PREFERRED EMBODIMENTS

Preferred embodiments of the invention are illustrated and described in connection with a stapler for applying staples to an exterior wound or incision across a layer of skin, although the invention is not limited to such a surgical stapler.

Figure 1:
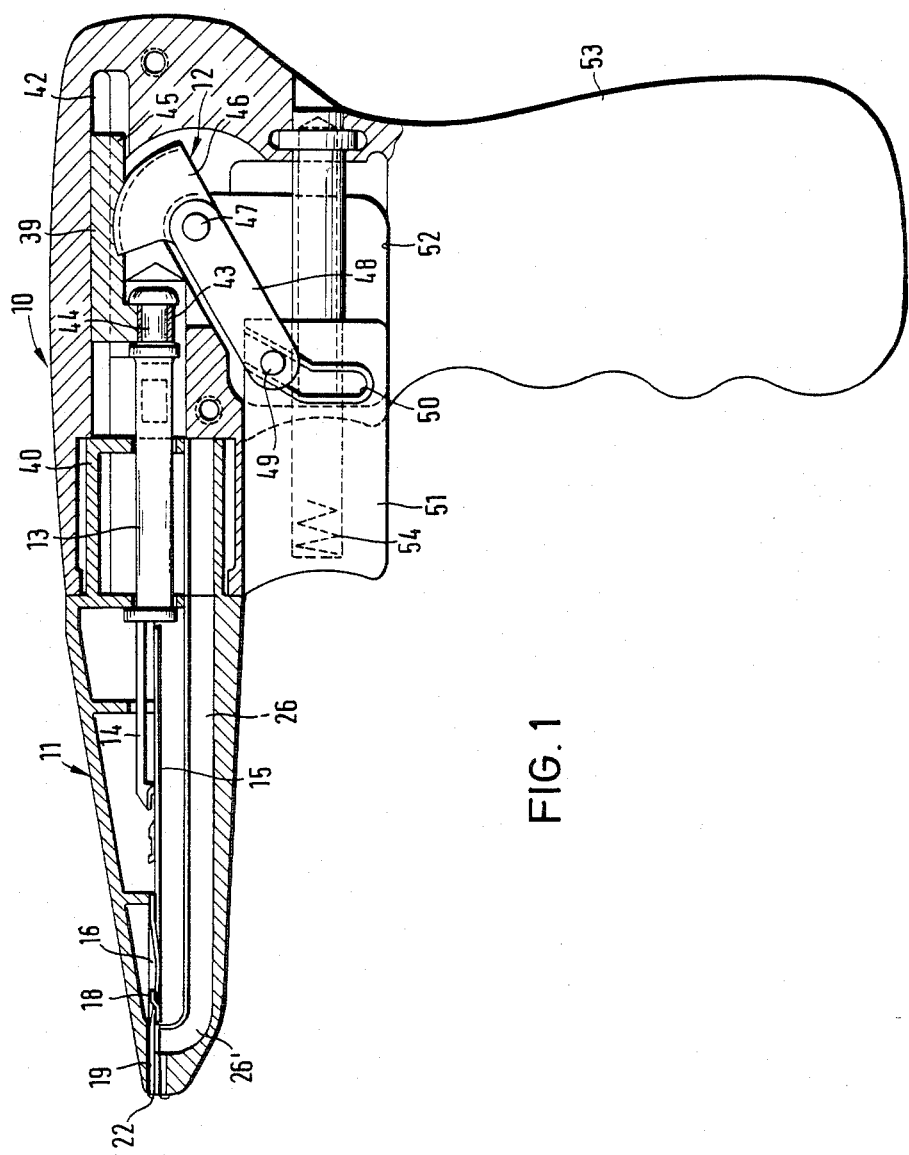
FIG. 1 is a schematic, longitudinal section view taken through a stapler according to the invention.

The embodiment of the stapler illustrated in FIGS. 1-9 comprises as depicted in FIG. 1, a rear housing portion 10 and a front housing portion 11. The front housing portion 11 is mounted to the rear housing position for rotation of the front housing portion about its longitudinal axis. The mechanism 12 for actuating the stapler is contained in the rear housing portion 10. A slide 13 which advances a driver 15 is guided in the front housing portion 11 for longitudinal displacement but is prevented from rotating. The slide 13 comprises a forwardly projecting flexible tongue 14 which also cooperates with the driver 15, as described more fully below. The driver 15 comprises an elongated rigid strip of material which is displaceable in its longitudinal direction in a channel or duct 16. The strip has a central recess 17 (FIG. 4) at the forward end of which is disposed a bent-up section 18 having an enlarged head.

A leaf spring 19 extends in the channel 16 substantially parallel to the driver 15. The leaf spring 19 has an inclined surface 20 (FIG. 2) and is provided with a central slot 21 (FIG. 4) closed on all sides which extends forwardly and rearwardly of the region of the inclined surface 20. The enlarged head of the bent section 18 of the driver 15 protrudes through the slot 21 and is pressed against the upper side of the leaf spring 19. The forward end of the leaf spring 19 is bent downwardly to form the anvil surface 22. The rear end of leaf spring 19 is fixed to the front housing portion 11.

Figure 2:
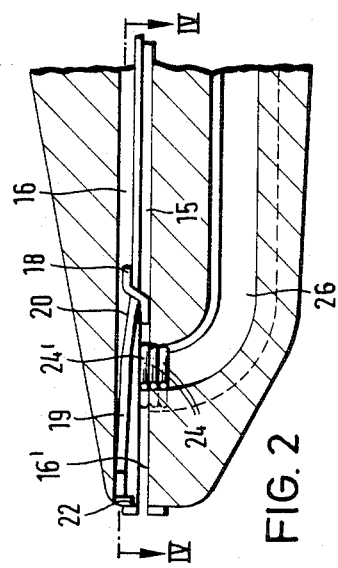
FIG. 2 is a longitudinal section view taken through the tip portion of the stapler of FIG. 1 depicting the anvil surface in its retracted position.

When the driver 15 is in its retracted position, as depicted in FIG. 2, the bent section 18 is positioned at the base of the inclined surface 20. Due to the inherent tension in the front region of the leaf spring 19, the leaf spring positions itself in the channel 16 as depicted in FIG. 2. Since the height of the channel 16 is greater than the height of the anvil 22, there is a clearance between the anvil 22 in its retracted position and the lower region 16' at the front of the channel 16.

Figure 4:
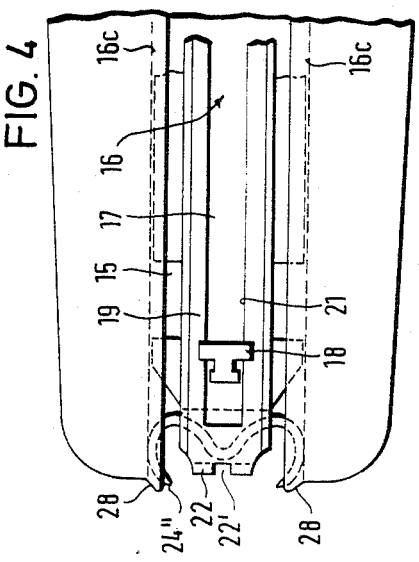
FIG. 4 is a section taken along line IV—IV of FIG. 2.
Figure 6:
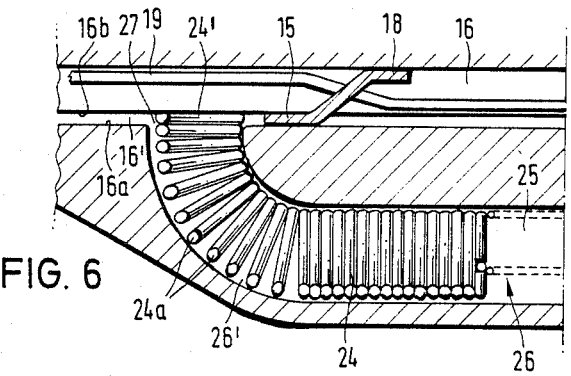
FIG. 6 is a vertical section view taken through the magazine portion of the stapler of FIG. 1.

A staple magazine 26 (FIGS. 1 and 6) extends parallel to the channel 16 in the front housing portion 11. Staples 24 are arranged in the magazine standing upright side by side and extending along the feed passage of the magazine parallel to the channel 16. A helical spring 25 braced against the housing contacts the rearmost staple and urges the rearmost staple and with it the entire stack of staples forward under constant tension. The forward section 26' of the staple magazine 26 is curved upwardly at an angle of 90° and opens into the channel 16. The staples are urged into the curved section 26' of the magazine and extend along the arc of the curve as depicted in FIG. 6, with the forwardmost staple 24' being disposed lying flat in the channel 16. The lower region 16' in the forward portion of the channel 16 in which the leaf spring 19 can move vertically is of greater width than the region above it. The height of the wider, lower channel portion 16' is only slightly greater than the thickness of the staples 24 so that channel portion 16' forms a guide channel for the advance of the forwardmost staple 24' and for the driver 15. This guide channel is defined by the lower guide face 16a, the two upper guide faces 16b, (FIG. 6), and by the lateral guide faces 16c (FIG. 4).

Figure 5:
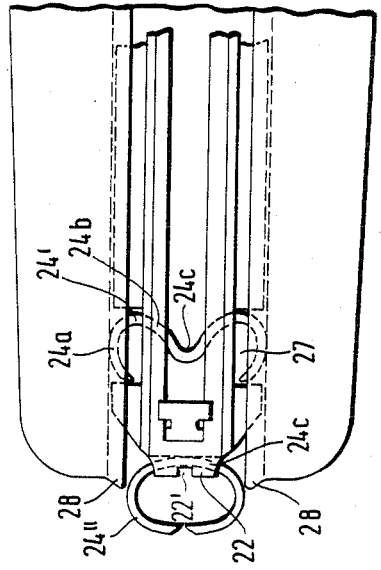
FIG. 5 is a section along line V—V of FIG. 3.

The staples 24, whose undeformed configuration is depicted in broken lines by the staple 24' in FIG. 5, have arcuate side portions 24a connected via a straight leg region 24b to a central base or crown portion 24c. The straight leg regions 24b extend obliquely outwardly from the base portion to the side portions 24a. The base portion 24c is semicircular with the circumference of the semicircle facing in the direction of the side portions. The base portion is engaged by the anvil surface 22 during forward motion of the staple. In order to insure centering of the staple 24, the anvil surface 22 is provided with a vertical slot 22'.

In the arcuate section 26' of the staple magazine 26, the side portions 24a of adjacent staples 24 are spaced apart while the straight leg regions 24b are in contact with adjacent leg regions due to the difference in radii of the curves for the upper and lower surfaces of the arcuate section 26'. Thus, the force of the spring 25 can be transmitted through the staples in the arcuate section 26' to the forwardmost staple 24'.

Figure 3:
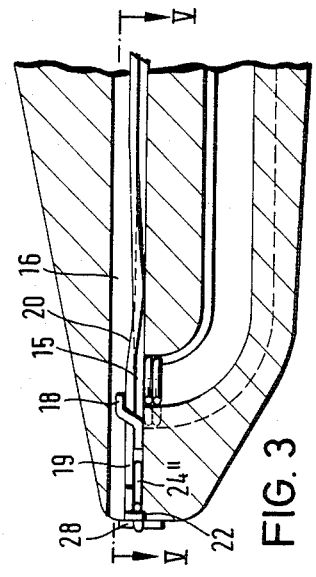
FIG. 3 is a view similar to that of FIG. 2 depicting the anvil surface in its operating position.

At the opening 27 (FIG. 5) of the magazine 26 into the channel 16, the underside of the upper guide face 16b is embossed (not shown) to hold the forwardmost staple 24' in a well-defined position. As the driver 15 is advanced from retracted position shown in FIG. 2, its front end abuts the forwardmost staple 24' and pushes it forward in the channel section 16'. At the same time, the bent section 18 moves along the inclined surface 20 of the leaf spring 19 so that the anvil surface 22 at the forward end of the leaf spring is brought from its retracted position into the operative position shown in FIG. 3. The staple designated 24" in FIGS. 3 and 4 is now situated between the forward end of driver 15 and the anvil surface 22 in a position in which the tips of the staple side portions protrude slightly forwardly from the instrument. As the driver 15 is advanced further, the staple side portions emerge from the front end of the instrument, with staple 24" being deformed and closed to the solid line configuration depicted in FIG. 5 in which the base 24c of the staple has been bent flat on the inner side of the anvil surface 22. To obtain as long a guide path as possible during deformation of staple 24", the guide faces 16a, 16b and 16c extend into projections 28 which define the exit gap of channel 16 out of the housing and which protrude slightly beyond the anvil surface 22.

As soon as the driver 15 has carried the forwardmost staple 24' away from the opening 27 of the magazine into the channel, the opening 27 is closed by the driver so that the next staple cannot be advanced into the channel 16. The next staple can only be advanced into the channel after the driver 15 has returned to its retracted position where it is clear of the opening 27.

Figure 7:
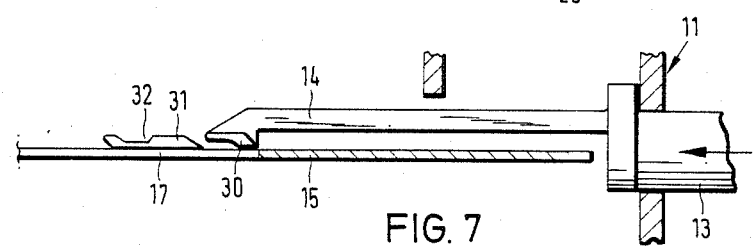
FIG. 7 is a side schematic view of a portion of the stapler of FIG. 1 illustrating the cooperation of the slide of the actuating mechanism and the driver as the driver is advanced.
Figure 8:
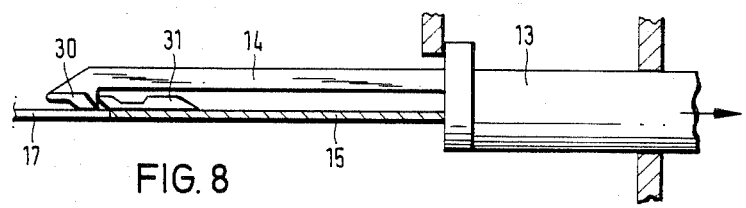
FIG. 8 is a side schematic view similar to that of FIG. 7 illustrating the cooperation of the slide and the driver of the stapler of FIG. 1 shortly before the driver is retracted.
Figure 9:
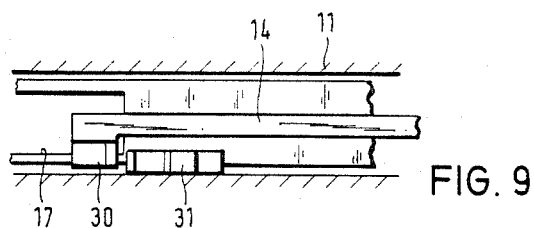
FIG. 9 is a plan schematic view of structure depicted in FIG. 8.

FIGS. 7-9 illustrate control of the driver 15 by the slide 13. Slide 13, which is supported in the front housing portion 11 for longitudinal displacement but is prevented from rotating, comprises at its forward end a forwardly projecting, flexible tongue 14 which is vertically spring-loaded. A laterally projecting guide wing or cam surface 30 is disposed at the end of the tongue 14 and cooperates with a control cam 31 fixed to the housing portion 11.

When the slide 13 is advanced by the actuating mechanism 12, its front face strikes driver 15, pushing it in the direction of the tool tip. A bevel formed on wing 30 causes wing 30 to abut on a rearward bevel of the control cam 31. The tongue 14 then flexes upwardly and wing 30 slides on the upper cam surface 32. If the slide 13 is retracted before its forward end position is reached corresponding to the operating position of the driver, the wing 30 slides back on to the upper cam surface 32, which maintains the slide and correspondingly the driver in the advanced position they assumed. Only after the slide 13 reaches the position shown in FIG. 8 and the wing 30 has gone beyond the front end of the control cam 31 is the stamping operation completed and staple 24" closed. As the slide 13 is thereafter being moved back, the rear surface of the wing 30, which is inclined, contacts the correspondingly inclined forward surface of the control cam 31. As a result, the tongue 14 is forced downward, and a projection of the tongue 14 enters into the slot 17 of the driver 15. As the slide 13 is further retracted, the wing 30 is pulled beneath the control cam 31, and the driver 15 is drawn rearward. Referring to FIG. 7, after the wing 30 has passed along the underside of the control cam 31, the tongue 14 springs upward, releasing the driver 15 at its starting position. Until the driver 15 is pulled back to its starting position, it does not clear the opening 27 of the staple magazine 26 into the channel 16.

Figure 10:
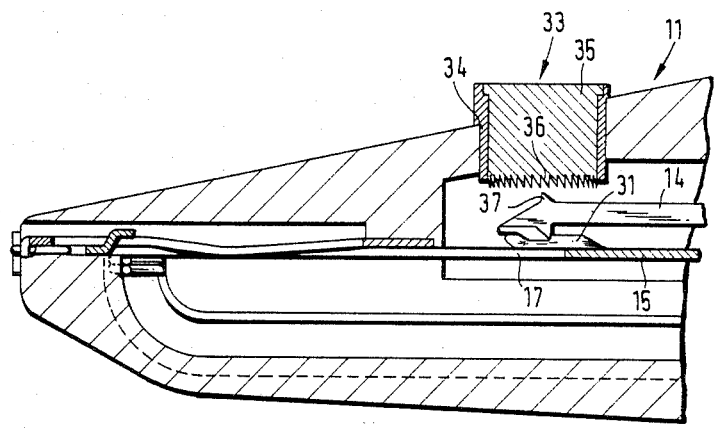
FIG. 10 is a vertical section view of a stapler tip including a counting mechanism according to another embodiment of the invention.

FIG. 10 depicts an embodiment in which a counting mechanism 33 is secured to the front housing portion 11. The counting mechanism is stepped by movement of the tongue 14 of the slide 13. The counting mechanism 33 comprises a hollow cylinder 34 fixed in the housing portion 11 in which is rotatably mounted a cylinder 35 having ratchet teeth 36 disposed about the periphery of the lower end thereof. A projection 37 disposed at the front end of tongue 14 engages the teeth 36 when the wing 30 is raised by the guide cam 31 during a feed movement. In this manner the cylinder 35 is rotated towards the forward end of the instrument by a predetermined angle with each feed movement of the driver 15. The top of the cylinder 35 is provided with a mark and the periphery of the hollow cylinder 34 is provided with a scale so that the mark indicates on the scale the number of staples 24 remaining in the magazine 26.

At the rear end of the front housing portion 11 is disposed a cylindrical bushing 40 (FIG. 1) in which slide 13 is coaxially mounted. The cylindrical bushing 40 can be removed from the rear housing portion 10 so that the magazine can be loaded with staples. The rear end of the slide 13 is coupled to a part 39 slidably movable along a track 42 in the interior of the rear housing portion 10. The sliding part 39 includes a sleeve 43 disposed about a shank 44 of the slide 13 which is bounded on both sides by flanges. The sliding part 39 is provided with a rack 45 having teeth or serrations which are engaged by corresponding serrations on a toothed disc segment 46. The toothed disc segment 46 forms one lever arm of a two-armed lever which pivots about a pivot pin 47 in the housing portion 10. The other lever arm 48 is engaged by a pin 49 disposed in a transverse slot 50 of a trigger lever 51. The trigger 51 is guided in a recess 52 of the handle 53 extending approximately parallel to channel 16, and is urged outwardly of the handle by a spring 54. Trigger 51 is dimensioned so that it can be actuated with the index finger when the handle 53 is gripped. The trigger, upon being pushed into the handle 53, causes the lever 46, 48, to be pivoted about the pivot pin 47 so that the sliding part 39 is advanced forwardly, and with it slide 13. Near the end position of the lever 46, 48 where it extends almost at right angles with the slide 13, leverage is the greatest, and corresponds to the stamping action of the driver. Thus, for a constant actuating force, the maximum force applied to the driver occurs during stamping.

Figure 11:
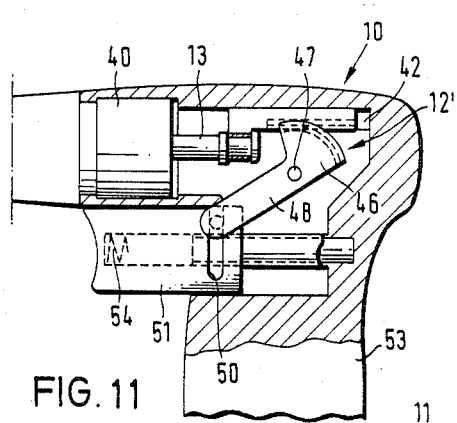
FIG. 11 is a vertical section view of a part of the rear housing of a stapler according to another embodiment of the invention depicting the actuating mechanism thereof in the retracted position of the slide.
Figure 12:
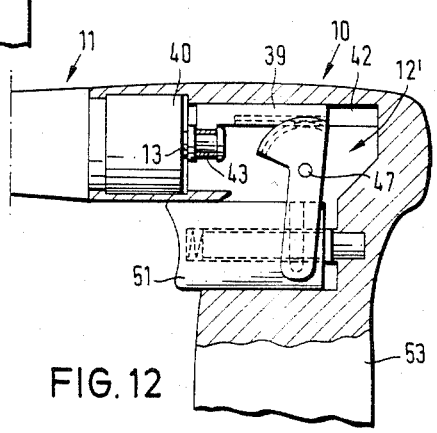
FIG. 12 is a view similar to that of FIG. 11 depicting the actuating mechanism in the feed position of the slide.

An actuating mechanism 12' similar to mechanism 12 of FIG. 1 is illustrated in FIGS. 11 and 12. FIG. 11 depicts the retracted position of the slide 13 and FIG. 12 its advanced position. Spring 54 urges the trigger 51 out of the handle 53 and at the same time brings the sliding part 39, and with it the slide 13, into the retracted position. In the embodiment of FIG. 1 the transverse slot 50 of the trigger 51 has an angular shape, while in the embodiment of FIGS. 11 and 12, the transverse slot 50 is straight.

Certain changes and modifications of the embodiments of the invention disclosed herein will be readily apparent to those skilled in the art. It is the applicants' intention to cover by their claims all those changes and modifications which could be made to the embodiments of the invention herein chosen for the purpose of disclosure without department from the spirit and scope of the invention.

What is claimed is:

1. A surgical stapler comprising a staple channel, a staple magazine for staples, means for advancing the staples in the staple magazine and delivering them to the staple channel, an anvil surface disposed at the end of the channel movable relative to the channel between an operating position and a retracted position, a driver displaceable in the channel relative to the anvil surface for deforming a staple in cooperation with the anvil surface, and a leaf spring to which the anvil surface is fastened, the leaf spring extending in the channel and having an inclined surface which cooperates with a projection on the driver for moving the anvil surface.

2. The stapler according to claim 1 wherein the staple magazine extends substantially parallel to the channel and comprises a curved section at its forward end opening into the channel.

3. The stapler according to claim 2 wherein the channel comprises side, upper and lower guide faces which guide movement of a staple lying flat in the channel.

4. The stapler according to claim 3 wherein the guide faces extend forward to beyond the anvil surface.

5. The stapler according to claim 4 wherein the stapler includes projections in which the guide faces extend forwardly beyond the anvil surface.

6. The stapler according to claim 1 wherein the anvil surface has a centrally-disposed notch or slot adapted to engage a staple disposed in the channel.

7. The stapler according to claim 1 and comprising a rear housing portion, an actuating mechanism for the driver disposed in the rear housing portion, and a front housing portion in which the driver and the anvil surface are rotatably disposed relative to the rear housing portion.

8. The stapler according to claim 7 wherein a slide is mounted in the stapler slidable in the longitudinal direction of the stapler with its forward portion in the front housing portion positioned to contact and move the driver and with its rear portion in the rear housing portion rotatably and slidably mounted therein and coupled to the actuating mechanism.

9. The stapler according to claim 8 wherein the actuating mechanism includes another sliding part rotatably coupled to the rear portion of the slide and guided in a track, and a lever pivotably disposed in the rear housing portion to engage and move the other sliding part upon pivoting of the lever.

10. The stapler according to claim 9 wherein the lever includes serrations and the other sliding part includes serrations which engage to move the other sliding part upon pivoting of the lever.

11. The stapler according to claim 9 wherein the mechanism comprises a trigger having an inoperative position and an actuated position, the lever being coupled to the trigger such that the effective leverage of the lever increases as the travel of the trigger increases from its inoperative to its actuated position and the force acting on the slide increases under a constant trigger actuating force as the trigger travel increases.

12. The stapler according to claim 1 wherein the driver clears the opening of the staple magazine into the channel only when the driver is in its fully retracted position.

13. The stapler according to claim 12 wherein a slide is mounted in the stapler slidable in the longitudinal direction of the stapler with its forward portion positioned to contact and move the driver and its rear portion coupled to an actuating mechanism.

14. The stapler according to claim 13 wherein the slide comprises a flexible tongue which is spring loaded in a direction transverse to the longitudinal direction of the stapler, and the housing includes a control cam cooperating with the tongue positioned such that the slide cannot be retracted until the tongue has been advanced to a predetermined location with respect to the cam.

15. The stapler according to claim 14 wherein the tongue of the slide is operative to retract the driver only after the latter has reached its operating position.

16. The stapler according to claim 14 and comprising a counting mechanism disposed in the housing, the tongue including a projection which engages and steps the counting mechanism.

* * * * *